(12) United States Patent
Schuetz et al.

(10) Patent No.: US 6,379,041 B1
(45) Date of Patent: Apr. 30, 2002

(54) X-RAY APPARATUS FOR PRODUCING A 3D IMAGE FROM A SET OF 2D PROJECTIONS

(75) Inventors: Oliver Schuetz, Erlangen; Matthias Mitschke, Nurernberg, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/532,073

(22) Filed: Mar. 21, 2000

Related U.S. Application Data

(63) Continuation-in-part of application No. 09/211,347, filed on Dec. 15, 1998, now Pat. No. 6,206,566.

(30) Foreign Application Priority Data

Nov. 2, 1998 (DE) .......................................... 198 50 494
Oct. 21, 1999 (DE) .......................................... 199 50 793

(51) Int. Cl.[7] .............................................. A61B 6/03
(52) U.S. Cl. ......................................... 378/205; 378/62
(58) Field of Search ............................. 378/4, 62, 63, 378/196, 197, 198, 205, 901

(56) References Cited

U.S. PATENT DOCUMENTS

| 5,706,324 A | 1/1998 | Wiesent et al. | 378/4 |
|---|---|---|---|
| 6,023,495 A | 2/2000 | Adler et al. | 378/4 |
| 6,028,907 A | 2/2000 | Adler et al. | 378/4 |
| 6,049,582 A | 4/2000 | Navab | 378/4 |
| 6,050,725 A | 4/2000 | Schmitz et al. | 378/62 |
| 6,079,876 A | 6/2000 | Schuetz | 378/205 |
| 6,206,566 B1 * | 3/2001 | Schuetz | 378/205 |

* cited by examiner

*Primary Examiner*—Drew Dunn
(74) *Attorney, Agent, or Firm*—Schiff Hardin & Waite

(57) ABSTRACT

An X-ray apparatus has an X-ray examination system with an X-ray source and an X-ray detector which can be displaced relative to a subject for the pickup of 2D projections, an arrangement for determining extrinsic imaging parameters and an arrangement for determining intrinsic imaging parameters, for determining the projection geometry in the examination system for each 2D projection, and having a control and computing stage for reconstructing 3D images from the 2D projections using the extrinsic and intrinsic imaging parameters. The arrangement for determining the intrinsic imaging parameters includes X-ray-positive marks which are allocated to the X-ray source and which are in the path of an X-ray beam emanating from the X-ray source, these marks following displacement of the X-ray system.

19 Claims, 5 Drawing Sheets

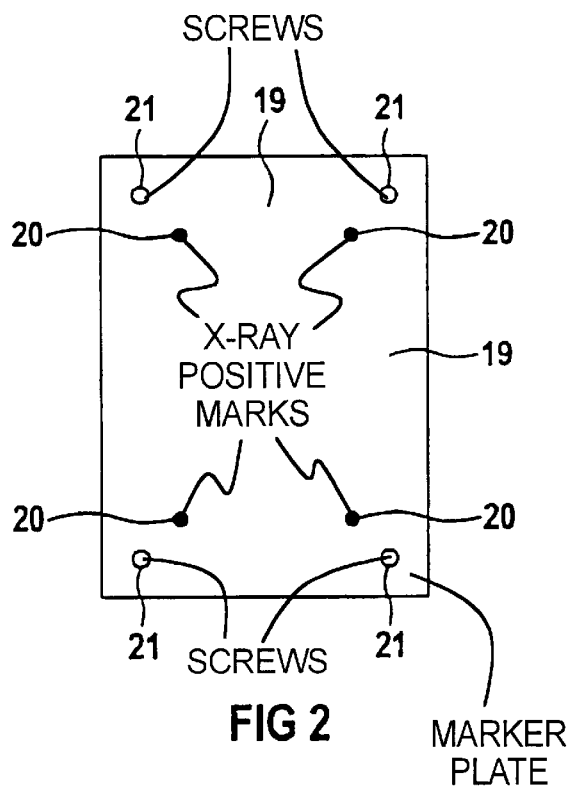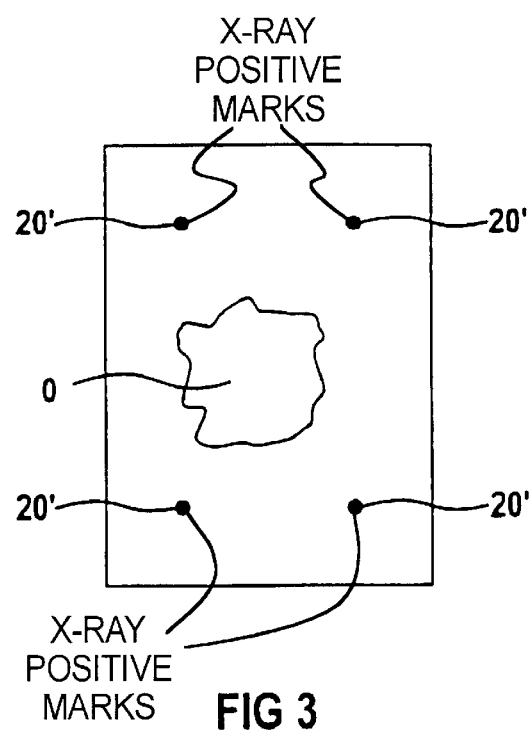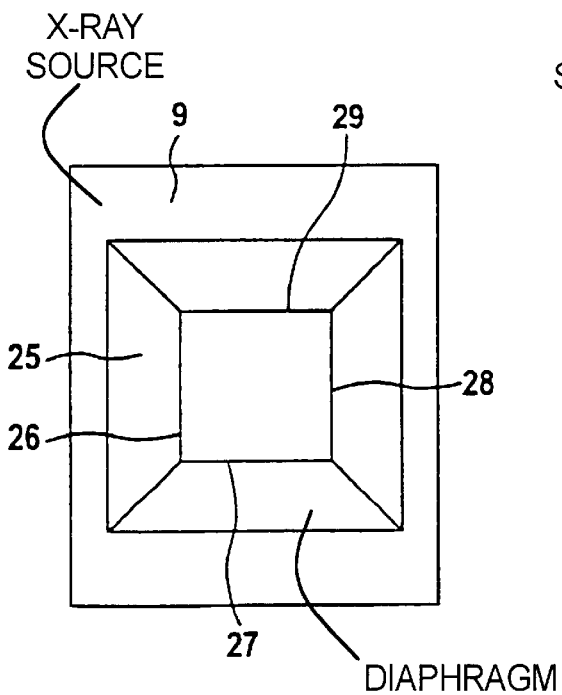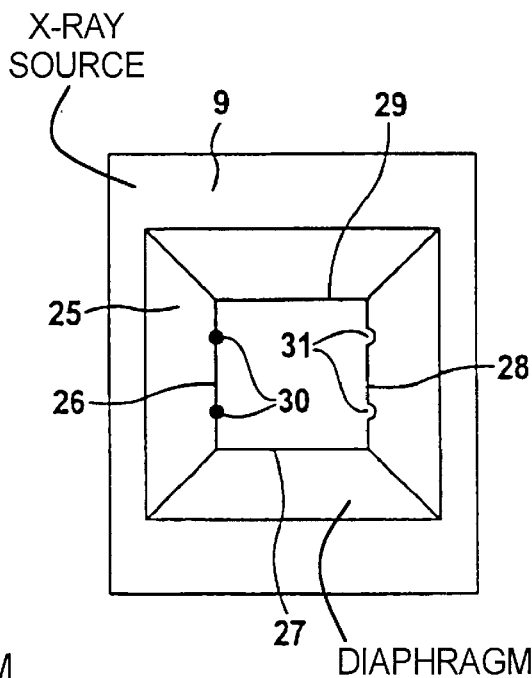

X-RAY APPARATUS FOR PRODUCING A 3D IMAGE FROM A SET OF 2D PROJECTIONS

RELATED APPLICATION

The present application is a continuation-in-part of U.S. application Ser. No. 09/211,347, filed Dec. 15, 1998, issued as U.S. Pat. No. 6,206,566.

BACKGROUND OF THE INVENTION

1. Field of the Invention

The present invention relates to an X-ray apparatus of the type having an X-ray examination system which with an X-radiation source and an X-ray detector which can be displaced relative to an examination subject for the pickup of 2D projections of a region of the subject, with subsequent reconstruction of 3D images of the region of the subject, as well as to a method for determining parameters that are required to reconstruct the 3D images in such an apparatus.

2. Description of the Prior Art

X-ray apparatuses of the above type commonly have a C-arm for mounting the X-ray source and the X-ray detector, the C-arm being mounted in a holding device such that it can be displaced in motorized fashion along its perimeter in a defined angle range (orbital motion). To obtain 2D projections from various projection angles for the reconstruction of 3D images—of a body region of a living organism, for example—in the pickup of the 2D projections of the body region of the organism, the C-arm is displaced along its perimeter subsequent to corresponding placement relative to the living organism to be examined. 3D images of the body region of the organism are subsequently reconstructed from the 2D projections captured with the X-ray examination system during the displacing motion. The reconstruction of 3D images is preconditioned by the precise knowledge of the projection geometries, i.e. the knowledge of the positions and orientations of the X-ray source and of the X-ray detector with respect to a stationary coordinate system during each of the individual 2D projections.

It has proven problematic that known stationary C-arm X-ray apparatuses, and quite particularly mobile C-arm X-ray devices, exhibit mechanical instabilities, particularly with respect to the displacement of the C-arm along its perimeter, so that the actual displacing motion of the X-ray examination system deviates from the ideal displacing motion due to torsional deformations and/or a slight "buckling" of the C-arm. Thus, the precision in the reproducibility of the projection geometries which is necessary for a reconstruction of 3D images cannot be achieved, particularly with the known mobile C-arm X-ray devices, for which reason additional position detection systems are necessary in order to be able to determine the projection geometries in every 2D projection.

For example, German OS 195 12 819 (corresponding to U.S. Pat. No. 5,706,324) teaches the utilization of a marker ring, usually made of plexiglass with inserted metal structures, which is arranged around the body region of the examined organism. The metal structures of the marker ring are visible in the 2D projections of the examined body region, so that the respective projection geometries of the 2D projections can be calculated from their position. This method has the disadvantage that the marker ring has a relatively large diameter, so that the distance between the X-ray source and the marker ring is very small (a few centimeters), particularly given mobile C-arm X-ray devices having a relatively small C-arm. The metal structures are thus imaged with significant enlargement in the 2D projections, so that large parts of the 2D projections are covered by the metal structures. Furthermore, only a small region of the metal structures of the marker ring is imaged in the 2D projections, so that the determination of the projection angle with the aid of the low number of imaged metal structures is difficult.

SUMMARY OF THE INVENTION

It is an object of the present invention to provide an X-ray apparatus of the abovementioned type, as well as a method for operating such an apparatus, wherein the determination of the projection geometries is simplified.

This object is inventively achieved in an X-ray apparatus with an X-ray examination system including an X-ray source and an X-ray detector which can be displaced relative to a subject for the pickup of 2D projections, with means for determining extrinsic and intrinsic imaging parameters, i.e. for determining the projection geometries of the X-ray system in each 2D projection, and with control and computing means for reconstructing 3D images from the 2D projections with the aid of the extrinsic and intrinsic imaging parameters, wherein the means for determining the intrinsic imaging parameters include X-ray-positive marks which are allocated to the X-ray source and which are arranged, in the path of an X-ray beam emanating from the X-ray source, these following the displacement motion of the X-ray system. For computing the projection geometries in each 2D projection, it is also necessary to provide means for determining extrinsic imaging parameters and means for determining intrinsic imaging parameters. The extrinsic imaging parameters describe the position and orientation of the focus of the X-ray source as a reference point, or the position and orientation of an arbitrarily selected zero point of the detector surface of the X-ray receiver as a reference point, for example, in a first stationary coordinate system. The intrinsic imaging parameters specify the geometric relation between the X-ray source and the X-ray detector—i.e., the distance of the X-ray source and the X-ray detector from one another, the orientation of the X-ray source and of the X-ray detector relative to one another, and the displacement of the X-ray detector perpendicular to the axis of the center beam of an X-ray beam emanating from the X-ray source, for example—in a second coordinate system, whose origin is preferably located at the reference point, i.e. at the focus of the X-ray source or at the zero point of the detector surface, for example. The intrinsic parameters also include the pixel size and the location of the image center. For each 2D projection, the position of the origin and the orientation of the second coordinate system—whose origin is located at the focus of the X-ray source, for example, and which, like the marks, is displaced relative to a subject together with the X-ray source in various 2D projections—are specified, by the extrinsic imaging parameters, as already noted.

In the examination of a subject, for each 2D projection of the subject, a matrix I of the intrinsic imaging parameters and a matrix E, which contains the extrinsic imaging parameters, are determined, whereby, according to P=I*E, a projection matrix P results for each 2D projection, each projection matrix P comprising the projection geometries of the corresponding 2D projection which are necessary for the reconstruction of 3D images. The projection matrices, which the control and computing means calculate from the extrinsic and intrinsic imaging parameters, are used for the reconstruction of 3D images from the 2D projections.

The means for determining the extrinsic imaging parameters are operable independent of the means of the intrinsic imaging parameters, so that the determination of the extrinsic and intrinsic imaging parameters is possible separately and thus is simplified in relation to the evaluated signals. The intrinsic imaging parameters are obtained using the X-radiation, with X-ray-positive marks which are arranged in one plane being allocated to the X-ray source such that they are imaged in the 2D projections. Since the geometric positions of the marks relative to each other and to the X-ray source are known in the second coordinate system, for example, whose origin is situated at the focus of the X-ray source, the intrinsic imaging parameters—i.e., the distance between the X-ray source and the X-ray detector, the orientation of the X-ray source relative to the X-ray detector, and displacement (if it occurs) of the X-ray detector perpendicular to the axis of the center beam of the X-ray beam emanating from the X-ray source—can be determined in simple fashion by the control and computing means, for example, using the distance relations of the marks, imaged in the 2D projections, relative to each other. It is particularly advantageous in the determination of the intrinsic imaging parameters that no additional sensor analysis is required at the X-ray apparatus.

According to a variation of the invention, the means for determining the extrinsic imaging parameters include a plate, which is arranged at the X-ray source or at the X-ray detector outside the path of the X-ray beam and which carries detectable structures or detectable optically active elements, and at least two image pick-up devices, such as cameras, which cooperate with the plate an which are stationary relative to the X-ray system. The plate is preferably arranged at the X-ray source in a geometrically specific fashion and preferably carries infrared light sources, whose positions can be detected by the cameras, as detectable optically active elements, for example. At least during the examination of a subject, the cameras are arranged in a geometrically specific fashion relative to the X-ray system, in the first stationary coordinate system. Using the camera images of the infrared light sources of the plate, which are picked up during a displacing motion of the X-ray system relative to a subject, the exact position of the plate—and thus, for example, of the focus of the X-ray source, which is simultaneously the origin of the second coordinate system—can be determined in the first stationary coordinate system. The calculation of the individual positions of the focus of the X-ray source in the course of an examination can ensue by a separate computer which is a component of the means for determining the extrinsic imaging parameters, or by the control and computing means of the X-ray apparatus. Known image analysis methods can be used for the evaluation of the camera images.

In an embodiment of the invention, the means for determining the extrinsic imaging parameters include an image pick-up device, which is arranged at the X-ray source or at the X-ray receiver, preferably outside the path of the X-ray beam, and structures or marks that can be detected using the image pick-up device, which are stationary relative to the X-ray system and preferably outside the path of the X-ray beam. The image pick-up device preferably is a camera which is arranged at the X-ray source or the X-ray receiver in a geometrically defined manner, for instance as calculated in a calibration measurement, and which picks up image information, during the displacement of the X-ray system, from the stationary structures or marks that are arranged in a geometrically defined manner relative to one another. Since the positions of the structures or marks in the first stationary coordinate system are known, for instance as a result of a calibration measurement, the positions of a reference point that is allocated to the X-ray source or to the X-ray receiver, which is the origin of the second coordinate system, with respect to which the imaging parameters are determined, can be determined based on the evaluating the structures or marks that are imaged in the captured camera images.

The means for determining the extrinsic imaging parameters alternatively may be transmit and receive system for electromagnetic waves or ultrasound waves, arranged outside the path of the X-ray beam. For example, by the defined attachment of a transmitter to the X-ray source and by the defined placement of a receiver in the first stationary coordinate system, the positions of the X-ray source, and thus of a reference point that is defined at the X-ray source, for instance the focus of the X-ray source, can be computed in the first coordinate system based on transit time measurements or phase measurements of electromagnetic waves or ultrasound waves. In a comparable manner, when respective transmitter and receiver systems are arranged at the X-ray source and/or at the X-ray detector in a defined manner in the first coordinate system, the positions of the X-ray source and/or of the X-ray detectors can be calculated.

In a particularly preferred embodiment of the invention the X-ray-positive marks are arranged in substantially planar fashion, i.e., they are all substantially disposed in one plane. In a version of this embodiment the marks are arranged in an X-ray-transparent marker plate which is allocated to the X-ray source such that it is penetrated by the X-ray beam in 2D pickups. The substantially planar marker plate is preferably arranged directly at the X-ray source and in the path of the X-ray beam emanating form the X-ray source. The distance between the marker plate and the focus of the X-ray source is about 200 mm. The marker plate thus always is located outside the work area of persons active at the X-ray means, and it does not limit the X-ray means in its functionality in any way. The exact position of the marks contained in the marker plate relative to the focus of the X-ray source, the positions of the marks in the second coordinate system, can be determined by a one-time calibration measurement with a calibrating cap on the marker plate. Furthermore, the geometric positions of the marks in the marker plate are known from the construction data for the production of the marker plate.

According to a variation of the invention, the marker plate carries at least three marks, which are arranged in the marker plate such that they can be imaged in different image corners or at different image margins of the 2D projections. In this way, the central tissue region of an examination subject to be imaged in the 2D projection is not superimposed by the imaged marks. Rather, the imaged marks are located in regions of a 2D projection which are usually less relevant for the diagnosis.

According to a further variation of the invention, the marks are of a spherical or rod-shaped design, resulting in clearly recognizable and evaluatable images of the marks in the 2D projections.

In another embodiment of the invention the X-ray source has a diaphragm which defines the cross-section of the X-ray beam and which has edges, the edges in the 2D projections representing the image margin, and the edges of the diaphragm fulfilling the function of linear marks. The advantage of this embodiment of the invention is that marks need not be additionally added to the X-ray apparatus and arranged in the path of the X-ray beam for the determination of the intrinsic imaging parameters; rather, an already existing structure of the X-ray apparatus, namely the diaphragm of the X-ray source, i.e., the edges of the diaphragm, serve as such marks. Since the positions of the edges of the diaphragm, which are situated substantially in one plane, relative to each other and to the focus of the X-ray source, i.e., their positions in the second coordinate system, are known or can be detected in a one-time calibrating process, the intrinsic imaging parameters can be determined with the aid of the imaging relations of the imaged edges, which can also be derived from the 2D projections, or the corner points formed by these edges.

According to another variation of the invention, the edges of the diaphragm can be provided with structures which can be imaged in the 2D projections. The structures can be spherical structures attached to the edges of the diaphragm, or of cutouts in the edges of the diaphragm.

Further variants of the invention provide that the X-ray source and the X-ray receiver are arranged at a C-ben or respectively, that the X-ray means is constructed mobile. The arranging of the X-ray source and the X-ray receiver at a C-bend that can be displaced along its perimeter advantageously makes possible diverse pick-up possibilities of radiological images of a subject. The mobile construction of the X-ray means permits the X-ray means to be used independent of location.

The above object of the invention also is achieved in a method for determining the intrinsic imaging parameters of an X-ray system, wherein the intrinsic imaging parameters are calculated during the pick-up of 2D projections of a subject. This approach is advantageous when the displacement motion of the X-ray system cannot be exactly reproduced. For example, given an arrangement of the X-ray source and the X-ray receiver at a C-arm, unreproducible displacement motions of the X-ray system are caused by unreproducible twisting or bending of the C-arm that occur during the displacement motion as a result of the gravitational force acting on the X-ray source and the X-ray receiver. In such a case, with each 2D projection of a subject the intrinsic imaging parameters should be recalculated online, that is, during the pick-up of a 2D projection of the subject, in order to be able to acquire high-quality images in the subsequent reconstruction of 3D images from the captured 2D projections.

If the displacement motion of the X-ray system can be reproduced, whether because the C-arm is so mechanically stable that it does not exhibit any deformation during displacement motions, or because in different displacement processes the deformations are always the same, then, the intrinsic imaging parameters are calculated in accordance with the inventive method in a calibrating procedure prior to the pick-up of 2D projections of a subject and these calculated parameters are stored in a storage unit of the X-ray apparatus. This procedure offers the advantage that the intrinsic imaging parameters need to be calculated only once, for instance upon installation of the X-ray apparatus, and they subsequently remain available for later reconstructions of 3D images from 2D projections of a subject that are obtained with the X-ray system.

The inventive method also includes steps for determining the extrinsic imaging parameters of an X-ray apparatus, with the extrinsic imaging parameters being calculated during the pick-up of 2D projections of a subject, in the case of unreproducible displacement motions of the X-ray source or of the X-ray receiver due to mechanical instabilities of the X-ray apparatus. Alternatively these extrinsic imaging parameters can be calculated in a calibrating procedure prior to the pick-up of 2D projections of a subject given a reproducible displacement motion of the X-ray source or of the X-ray receiver.

DESCRIPTION OF THE DRAWINGS

FIG. 2 is a view, as seen in the direction of arrow II in FIG. 1, of the marker plate of the X-ray apparatus from FIG. 1.

FIG. 3 shows a 2D projection with imaged marks of the marker plate from FIG. 2.

FIG. 4 illustrates an X-ray source from FIG. 1, with a diaphragm.

FIG. 5 illustrates an X-ray source from FIG. 1, with a diaphragm provided with structures that can be imaged.

DESCRIPTION OF THE PREFERRED EMBODIMENTS

Figure 1:
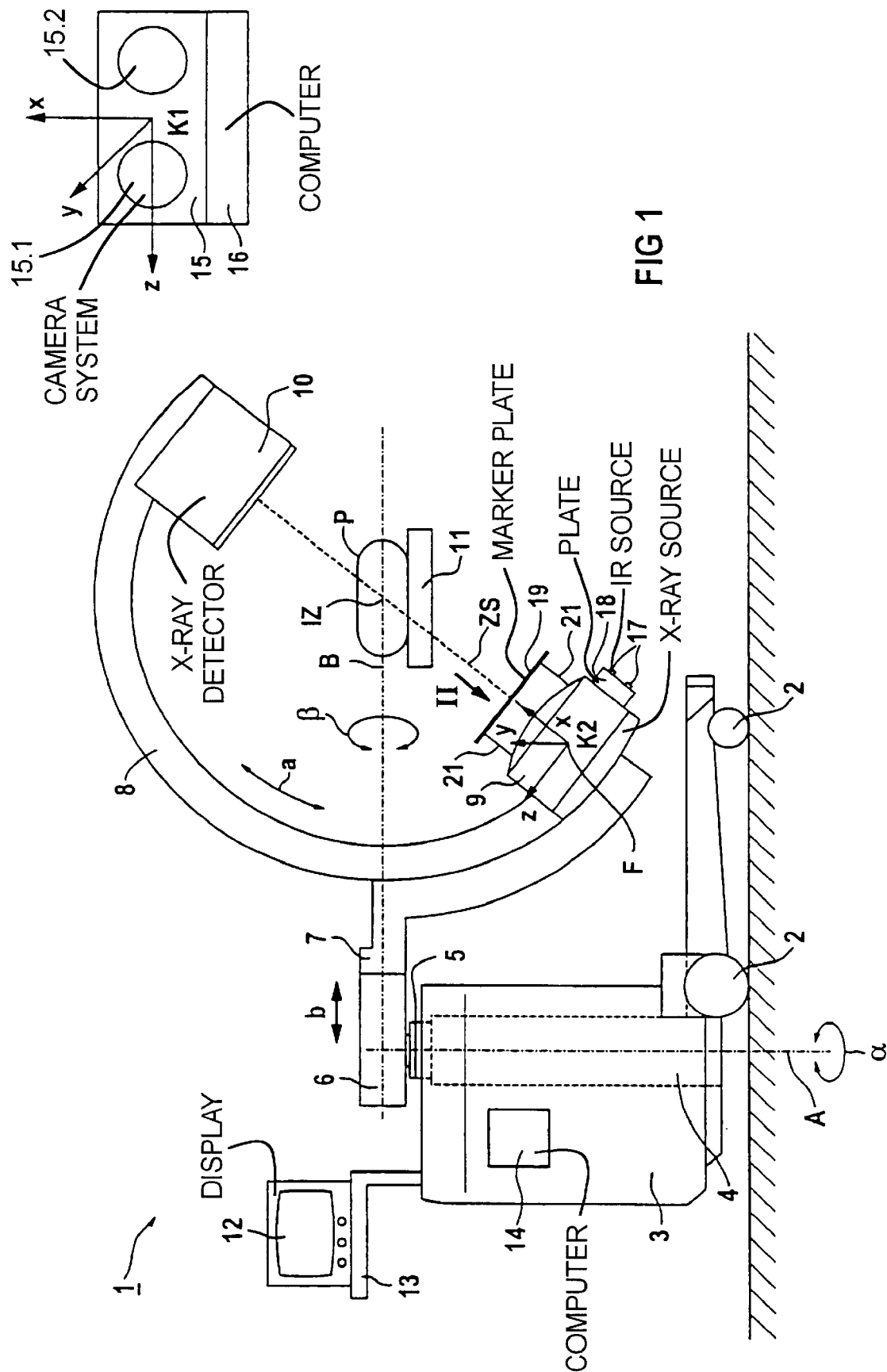
FIG. 1 is a side view of a first embodiment of an inventive X-ray apparatus with a camera system for determining extrinsic imaging parameters.

In an exemplary embodiment, the inventive X-ray apparatus depicted in FIGS. 1 and 6–8 is a C-arm X-ray device 1 with a device cart 3 that can be driven on wheels 2. The C-arm X-ray device 1 has a lifting device 4, which is depicted in FIG. 1 only schematically, with a column 5 having a longitudinal axis A around which the column 5 can be rotated in the direction of the double arrow α. A holder 6 is arranged at the column 5, a mount 7 being in turn arranged at the holder 6 for mounting a C-arm 8, which has an isocenter IZ. The C-arm 8 carries an X-ray source 9 and an X-ray detector 10, which are disposed opposite each other at the respective ends of the C-arm 8 and which are arranged relative to one another such that a center beam ZS, emanating from the X-ray source 9, of an X-ray beam proceeds through the isocenter IZ of the C-arm 8 and strikes the X-ray receiver 10 approximately in the middle. The C-arm 8 is mounted at the mount 7 such that it can be displaced along its perimeter in motorized fashion in the direction of the double arrow a, in a manner not depicted. The mount 7 is mounted at the holder 6 such that it is rotatable about a common axis B of the holder 6 and the mount 7 (cf. double arrow β, angulation) and displaceable in the direction of the axis B (double arrow b). The C-arm 8, which is connected to the column 5 of the lifting device 4 via the mount 7 and the holder 6, can be displaced vertically relative to the device cart 3 with the aid of the lifting device 4.

In the exemplary embodiment, the C-arm X-ray device 1 is provided for the creation of 3D images of a body region of a patient P, depicted only schematically in FIG. 1, who is lying on a patient bed 11. The 3D images are reconstructed from 2D projections of the body region from different angles which are obtained with the aid of the X-ray examination system, which is comprised of the X-ray source 9 and the X-ray detector 10, and the images can be displayed on a display device 12 arranged on a holder 13 of the C-arm X-ray device 1.

To pick up the 2D projections from various projection angles, the C-arm 8, which carries the X-ray examination system, is displaced in motorized fashion along its perimeter, in the direction of the double arrow a, through an angle range greater than 180° around the examined and displayed body region of the patient P. Approximately 50 to 100 2D projections of the body region of the patient P are picked up with the X-ray system from different angles of projection during the displacing motion.

The reconstruction of 3D images from the 2D projections ensues with control and computing means of the X-ray device 1 in the form of an efficient computer 14. The computer 14 not only performs the reconstruction of 3D images, but also controls the motorized displacing motion of the C-arm 8 and the pickup of 2D projections by the X-ray examination system. The computer 14 can be a multiprocessor system which permits parallel calculations, which shorten the calculation time. The computer 14 need not necessarily be integrated in the C-arm X-ray device 1, but can be constructed as an external computer which is correspondingly connected to the C-arm X-ray device 1.

As stated above, for the reconstruction of 3D images from 2D projections, the precise knowledge of the projection geometries, i.e., knowledge of the positions and the orientations of the X-ray source 9 and of the X-ray detector 10, is required for each 2D projection. The projection geometries can be expressed in intrinsic and extrinsic imaging parameters.

In the exemplary embodiment, the extrinsic imaging parameters specify the position and the orientation of the focus F of the X-ray source 9—as the origin of a second coordinate system K2, which is moved together with the X-ray source 9—in a stationary coordinate system K1, whose position and orientation is defined in the exemplary embodiment by the means for determining the extrinsic imaging parameters. The selection of the coordinate system K1 is arbitrary; i.e., the origin and the orientation of the coordinate system K1 can be defined differently.

In the exemplary embodiment, the means for determining the extrinsic imaging parameters include a camera system 15 (which comprises at least two cameras 15.1 and 15.2), a computer 16, and a plate 18, which is provided with an infrared light source 17 and is arranged at the X-ray source 9. The camera system 15, which can pick up infrared signals, is arranged in a geometrically specific fashion in the stationary coordinate system K1, at least during an examination procedure. The camera system 15 is oriented with respect to the C-arm X-ray device 1 such that all motions of the C-arm 8 are conducted within its field of view. The camera system 15 thus can visually detect the infrared signals emitted by the infrared light sources 17 during a displacing motion of the C-arm 8 along its perimeter. The evaluation of the camera images picked up during the displacing motion of the C-arm 8 is undertaken by the computer 16. Using the camera images, the computer 16 calculates the respective positions and orientations of the plate 18 in relation to the first coordinate system K1. These data are made available to the computer 14 of the C-arm X-ray device 1 by the computing means 16 via signal lines (not depicted in FIG. 1) or telemetrically. Since the plate 18 is arranged in a geometrically specific fashion relative to the X-ray source 9, or to the focus F of the X-ray source 9, the computer 14 using this data can always detect the current position of the focus F of the X-ray source 9, and thus the position of the origin of the second coordinate system K2, in each 2D projection. For every 2D projection, this results in a matrix E which contains the extrinsic imaging parameters of the respective 2D projection. The matrices E with the extrinsic imaging parameters for the various 2D projections are respectively set up in real time.

The intrinsic imaging parameters—which specify the distance of the X-ray source 9 from the X-ray detector 10, the orientation of the X-ray source 9 relative to the X-ray detector 10, and a possible displacement of the X-ray detector 10 perpendicular to the axis of the center beam ZS of the X-ray beam emanating from the X-ray source 9—are detected using a marker plate 19. The marker plate 19 is arranged directly at the X-ray source 9, specifically in the path of an X-ray beam which emanates from the X-ray source 9. In the exemplary embodiment, the marker plate 19, which is constructed of an X-ray-permeable material such as plexiglass, is provided with four X-ray-positive spherical marks 20. The marks 20 are arranged in the marker plate 19 such that they are situated in different image corners or at different image margins of the 2D projections that are picked up with the aid of the X-ray detector 10. In this way, the body regions of an examined patient P which are imaged in the 2D projections are not superimposed by the imaged marks 20'. Should the imaged marks 20' prove disturbing in the 2D projections, the imaged marks 20' can subsequently be calculated out of the 2D projections in an image processing step on the basis of the position and size of the imaged marks 20', which are known from the intrinsic imaging parameters, and on the basis of the known X-ray absorption of the marks 20.

In the exemplary embodiment, the determination of the intrinsic imaging parameters from the marks 20', imaged in the 2D projections, occurs with reference to the second coordinate system K2, whose origin is situated at the focus F of the X-ray source 9. The positions of the marks 20 are known, or can be detected with a one-time calibration process, in the second coordinate system K2. The relative positions of the marks 20 in the marker plate 19 are also known from the construction data of the marker plate 19. The evaluation of the 2D projections is made by the computer 14, which determines the intrinsic imaging parameters using the known geometric positions of the marks 20 in the second coordinate system K2 and the distance relations of the imaged marks 20' in the 2D projections. This is accomplished by means of suitable pattern detection. Thresholding methods, cross-correlation, template matching and segmenting methods, such as are known and used in imaging analysis, are possible methods. For each 2D projection, the intrinsic imaging parameters are combined in a matrix I in real time. A projection matrix P is ultimately obtained, in real time, from the matrices E and I for each 2D projection. The projection matrices P are used for the reconstruction of 3D images by the computer 14.

FIG. 2 shows the marker plate 19 from FIG. 1, which is provided with the marks 20, in the direction of the arrow II in FIG. 1. In the exemplary embodiment, the marker plate 19 is fastened to the X-ray source 9 with screws 21. The marker plate 19 can also be fastened to the X-ray source 9 by means of clamps or other suitable fixing elements. FIG. 3 depicts the marks 20' of the marker plate 19 that are imaged in the corners of a 2D projection and that are not superimposed on an imaged subject O.

Beyond this, the marks 20 need not necessarily be arranged in a marker plate 19. The marks 20 need only be allocated to the X-ray source 9 such that they are located in the path of an X-ray beam which emanates from the X-ray source 9 and are substantially situated in one plane, whereby their positions relative to each other are known or can be detected easily.

Moreover, instead of spherical marks, rod-shaped marks or differently shaped marks which can be imaged clearly in X-ray images can be used for the determination of the intrinsic imaging parameters.

In the exemplary embodiment, the plate 18 of the means for determining the extrinsic imaging parameters is arranged at the X-ray source 9. However, the plate 18 can also be arranged at the X-ray detector 10. In this case, it is appropriate to place the origin of the second coordinate system K2, with reference to which the intrinsic imaging parameters are specified, at an arbitrarily selectable reference point of the X-ray detector 10, which can be the midpoint of the detector surface of the X-ray detector 10, for example. The origin of the second coordinate system K2 need not necessarily be located on or in the detector surface, however. The origin of the second coordinate system K2 can also be clearly defined given such an arrangement of the plate 18 at the X-ray detector 10. In this case, as in the manner described above, the intrinsic imaging parameters can be determined using the distance relations of the marks 20' which are imaged in the 2D projections, it being possible to derive these relations using the 2D projections and to define them with reference to the second coordinate system K2, with the geometric positions of the marks 20 in the marker plate 19, which is allocated to the X-ray source 9, relative to each other and relative to the X-ray source 9, or to the focus F of the X-ray source 9, being known.

Furthermore, the plate 18 need not necessarily carry infrared light sources 17. Rather, the plate 18 can be provided with mechanical structures or other elements, preferably optically active elements, which enable the position determination of the plate 18 with the aid of camera images.

In the means for determining the extrinsic imaging parameters, the cameras 15.1 and 15.2 need not necessarily be integrated in a system. Rather, individual cameras can be used to calculate the extrinsic imaging parameters, whose relative positions must be known, or must be determined.

FIG. 4 depicts an illustration of the X-ray source 9 from FIG. 1 as seen in the direction of the arrow II from FIG. 1, whereby the marker plate 19 has been removed from the X-ray source 9. A diaphragm 25 of the X-ray source 9, which is present in each X-ray source per se, is further detailed in FIG. 4. The diaphragm 25 serves to limit the cross-section of the X-ray beam emanating from the X-ray source 9 such that only such X-ray quanta as can strike at the detector surface of the X-ray detector 10 leave the X-ray source 9. The edges 26 to 29 of the diaphragm 25 are imaged in the 2D projections and form the image margin. In the exemplary embodiment, the edges 26 to 29 of the diaphragm 25, which are imaged in the 2D projections, are applied in the determination of the intrinsic imaging parameters, the imaged edges 26 to 29 serving the function of linear marks. Since the edges 26 to 29 are situated substantially in one plane, and the geometric positions of the edges 26 to 29 of the diaphragm 25 relative to one another are known, and the relative positions of the edges 26 to 29 in the second coordinate system K2—which, in the case of the exemplary embodiment, has its origin at the focus F of the X-ray source 9—can also be detected without difficulty, in a calibrating procedure. For example, the intrinsic imaging parameters can also be determined with the aid of the distance relations of the edges 26 to 29 of the diaphragm 25, which are imaged in the 2D projections. The advantage of this embodiment of the invention is that additional X-ray-positive marks need not be provided at the X-ray source 9 in order to be able to determine the intrinsic imaging parameters. The corners in the 2D projections formed by the edges 26 to 29 can be used for the evaluation, for example.

As depicted in FIG. 5, the edges 26 to 29 of the diaphragm 25 can be provided with additional structures that can be imaged, such as X-ray-positive marks 30 or detectible cutouts 31, it being possible to use these for the determination of the intrinsic imaging parameters as prominent points in the 2D projections.

The evaluation of the 2D projections comprising the imaged edges 26 to 29 of the diaphragm 25, or structures 30, 31, ensues analogously in the manner described above.

Figure 6:
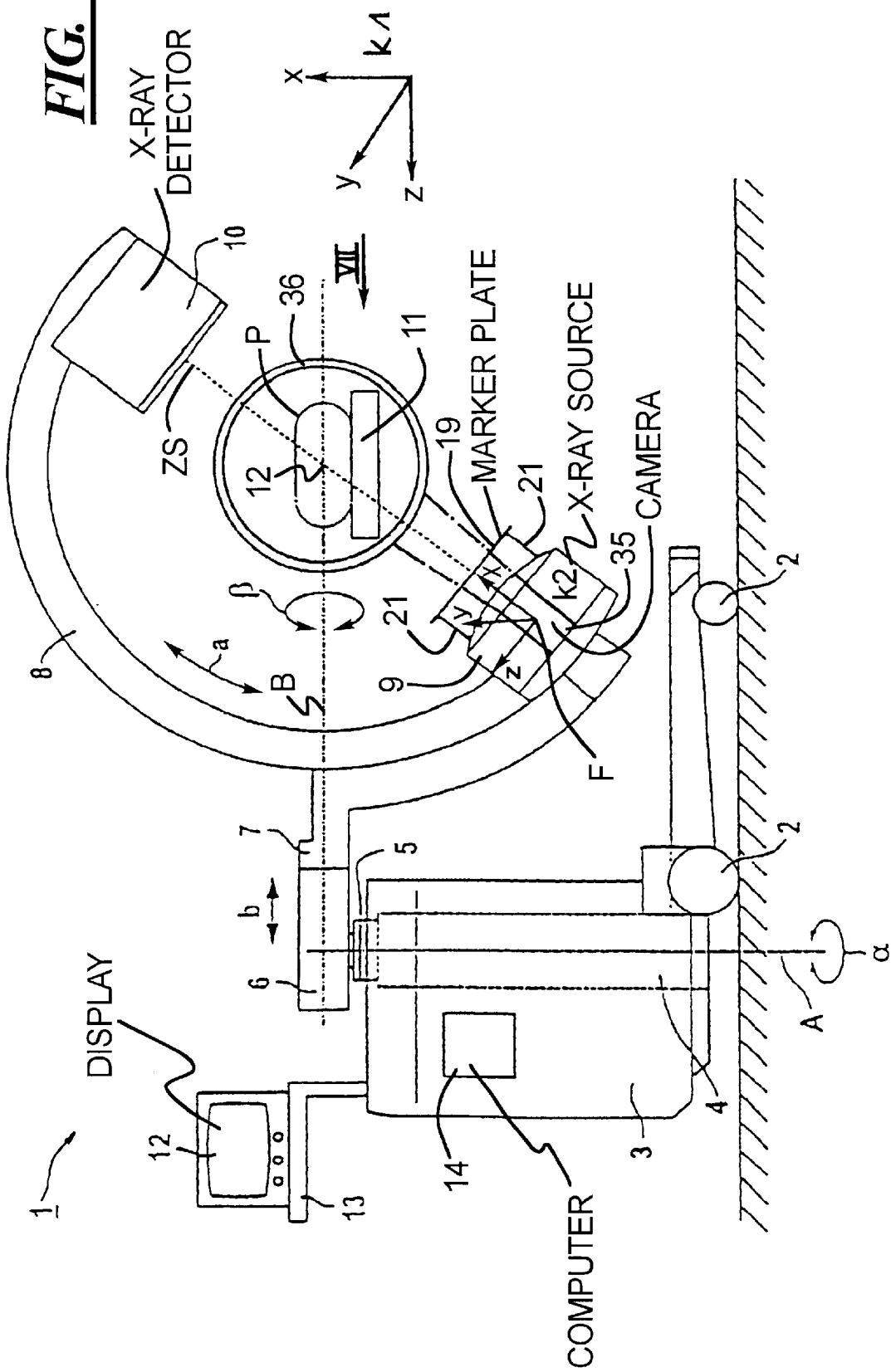
FIG. 6 is a side view of a second embodiment of an inventive X-ray apparatus with an optical marker ring for purposes of determining the extrinsic imaging parameters.
Figure 7:
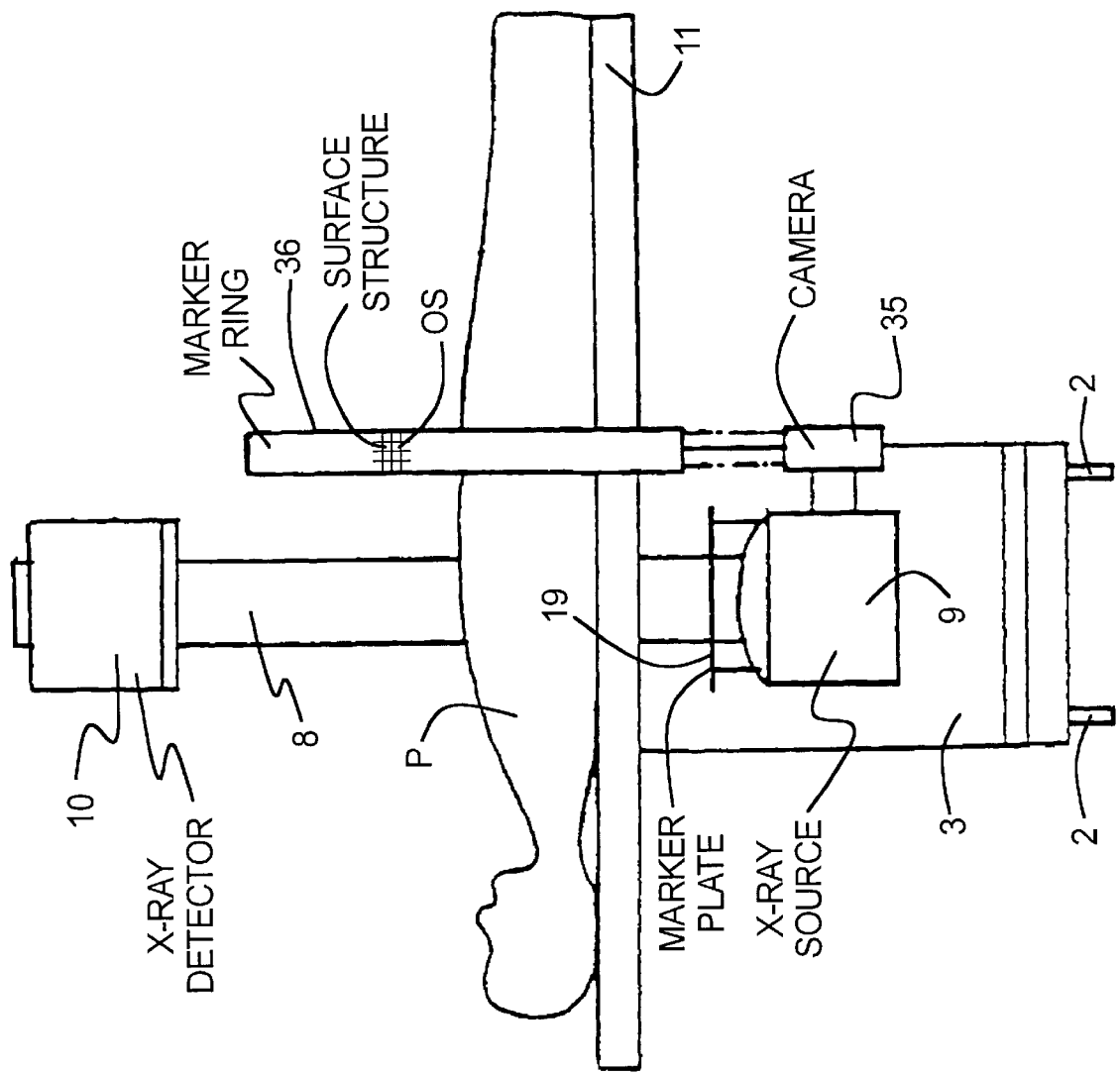
FIG. 7 shows a simplified view of the apparatus of FIG. 6 in the direction of the arrow VII in FIG. 6.

FIGS. 6 and 7 illustrate a second exemplary embodiment of an inventive X-ray apparatus. Components of the X-ray apparatus that is illustrated in the FIGS. 6 and 7 having substantially the same structure and function as components of the X-ray apparatus that is illustrated in FIG. 1 are provided with the same reference characters.

Unlike the X-ray apparatus illustrated in FIG. 1, the X-ray apparatus illustrated in FIGS. 6 and 7 does not have a plate 18 that is arranged at the X-ray source 9 or a camera system 15, but instead has an image pick-up device in the form of a camera 35 that is secured at the X-ray source 9, laterally outside the beam path of the X-ray beam, that is directed at a marker ring 36, which is likewise arranged outside the X-ray beam emanating from the X-ray source 9. The marker ring 36 surrounds the patient P and is secured at the patient bed 11 in this embodiment. The marker ring 36 need not necessarily be secured at the patient bed 11; it is only necessary that it not move during an examination of the patient P. Along its outer perimeter, the marker ring 36 is provided with surface structures OS that are created in a defined, i.e., systematic, manner, these being depicted only schematically. The camera 35 is arranged at the X-ray source 9 in a defined manner and is oriented to the marker ring 36 so as to be able to pick up the surface structures OS of the marker ring 36 that lie in its field of view. The position of the camera 35 relative to the X-ray source 9, particularly relative to the focus of the X-ray source 9, which coincides with the origin of the second coordinate system K2, is known, as is the position of the marker ring 36 in a first stationary coordinate system K1 that is provided for specifying the positions of the X-ray source 9. Therefore, given displacement motions of the X-ray system, the surface structures OS of the marker ring 36 that are picked up by the camera 35 allow the positions of the focus F of the X-ray source 9 and thus of the origin of the second coordinate system K2 to be determined, with respect to which the intrinsic imaging parameters are calculated, as described above, in a first coordinate system K1. Of course, it is also possible to calculate the extrinsic imaging parameters of the X-ray means with the camera 35 arranged at the X-ray source 9 in a defined manner and with the marker ring 36.

The camera 35 need not necessarily be arranged at the X-ray source 9, but can also be arranged at the X-ray receiver 10. If the camera 35 is arranged at the X-ray receiver 10, whereby, in this case, an arbitrarily selected zero point on the detector surface of the X-ray receiver 10 should be used as a reference point for defining the origin of the second coordinate system K2.

Furthermore, the detectable structures OS need not necessarily be arranged on a marker ring. A different type of phantom that is provided with optically detectable structures and that is arranged outside the beam path of the X-ray beam can be used for determining the extrinsic imaging parameters. The structures or marks that are to be picked up optically using the camera 35 need not necessarily be located in the vicinity of the patient, but can be arranged at a small distance from the patient, though the structures must be in the pick-up range of the camera 35 that is arranged at the X-ray source 9 or at the X-ray detector 10.

Figure 8:
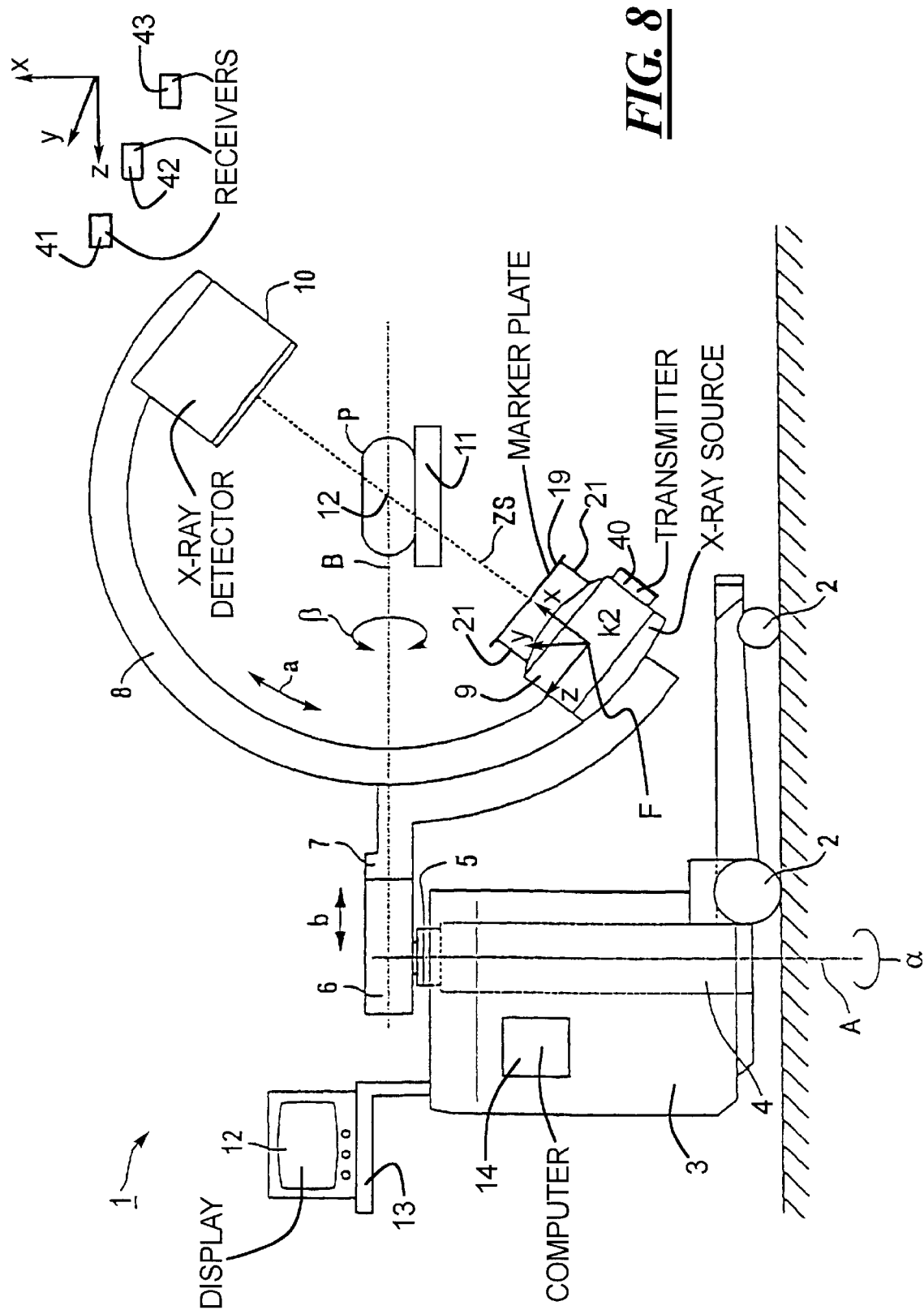
FIG. 8 is a side view of a third embodiment of an inventive X-ray apparatus with a transmitting and receiving apparatus for determining the extrinsic imaging parameters.

FIG. 8 depicts a third embodiment of an inventive X-ray apparatus, wherein components of the X-ray apparatus illustrated in FIG. 8 that have the same structure and function as those illustrated in FIG. 1 are likewise provided with the same reference characters.

Unlike the X-ray apparatus depicted in FIG. 1 and unlike the apparatus depicted in FIGS. 6 and 7, for determining the extrinsic imaging parameters the X-ray apparatus depicted in FIG. 8 has a transmitting and receiving arrangement for electromagnetic waves. In the exemplary embodiment, a transmitter 40 for emitting electromagnetic signals is arranged at the X-ray source 9 in a defined manner relative to the focus F of the X-ray source 9, which represents the origin of the second coordinate system K2 that is used for defining the intrinsic imaging parameters. Furthermore in the exemplary embodiment, three receiver 41 to 43 are arranged in a geometrically defined manner in the first coordinate system K1. By the emission of electromagnetic waves by the transmitter 40 during displacement motions of the X-ray system, and by receiving the electromagnetic waves by the receivers 41 to 43, the positions of the focus F of the X-ray source 9 are unambiguously determined, for instance by measuring the transit time or phase of the electromagnetic waves. The calculation of the positions can be accomplished by the control and computing unit 14, for example, which can be connected to the receivers 41 to 43 (such a connection not being explicitly shown in FIG. 8).

Analogously, given the arrangement of a transmitter at the X-ray receiver 10, the position of a reference point of the X-ray receiver 10 during the displacement motions of the X-ray system can be calculated.

Instead of a transmitter, at least one receiver can be arranged at the X-ray source 9 in a defined manner or at the X-ray detector 10, and at least one transmitter can be arranged in a defined manner in the first stationary coordinate system K1. If, for example, three transmitters are arranged in a defined manner in the first coordinate system K1, and one receiver is arranged in a defined manner at the X-ray source 9, then the position of the focus of the X-ray source 9 can be unambiguously determined in the first coordinate system K1 given displacement motions of the X-ray system by measuring the transit time of electromagnetic waves.

As an alternative to electromagnetic waves, it is possible to use ultrasound waves.

The intrinsic and extrinsic imaging parameters, can be acquired and stored online, that is, simultaneous to the pick-up of 2-D projections of a subject, or offline, that is, in a (usually) one-time calibrating procedure in the process of bringing the X-ray means into operation.

Offline determination of the intrinsic and extrinsic imaging parameters is possible when the motions of the X-ray system in the pick-up of 2D projections are reproducible. As compared to the offline calculation of the intrinsic imaging parameters for the described exemplary embodiments, this means that in the displacement motions along its perimeter, the C-arm does not exhibit any deformations, or always exhibits the same reproducible deformations. Relative to the offline calculation of the extrinsic imaging parameters, this means that the support of the C-arm 8 is so stable that it is possible to reproduce the displacing motions of the C-arm 8, and thus the locations of the X-ray source 9 and of the X-ray receiver 10 given repeated identical displacement.

If the X-ray apparatus does not exhibit such a stable behavior or exhibits a behavior which is only partly stable, that is, as to the C-arm deformations or to the displacement of the C-arm, then the imaging parameters that relate to or are affected by the unstable system behavior should always be determined online, in order to be able to construct high-quality 3D images with the aid of the imaging parameters.

The exemplary embodiments depicted in the figures and described above can be employed for the determination of the intrinsic imaging parameters either alternatively to each other or in combination.

The invention has been described on the basis of the example of a C-arm X-ray device 1, however, the invention is not limited to use in mobile C-arm X-ray devices, but is also usable in stationary X-ray devices.

Although modifications and changes may be suggested by those skilled in the art, it is the intention of the inventors to embody within the patent warranted hereon all changes and modifications as reasonably and properly come within the scope of their contribution to the art.

We claim as our invention:

1. An X-ray apparatus comprising:
    an X-ray examination system having an X-ray source which emits an X-ray beam from a focus and an X-ray detector on which said X-ray beam is incident;
    means for displacing said X-ray examination system relative to an examination subject while irradiating said examination subject with said X-ray beam from a plurality of different projection angles for obtaining a plurality of 2D projection images of said examination subject respectively at said plurality of different projection angles, each of said 2D projection images having a unique projection geometry associated therewith;
    means for determining extrinsic imaging parameters and means for determining intrinsic imaging parameters for each of said 2D projection images, for determining the respective projection geometries for said 2D projection images, said means for determining intrinsic imaging parameters comprising a plurality of X-ray positive marks disposed in a path of said X-ray beam, said X-ray positive marks following displacement of said X-ray examination system; and
    a computer using said 2D projection images and said projection geometries for constructing a 3D image therefrom of said examination subject.

2. An X-ray apparatus as claimed in claim 1 wherein said means for determining extrinsic imaging parameters include a plate mounted on one of said X-ray source and said X-ray detector outside of said path of said X-ray beam, said plate carrying a plurality of detectable items, and two stationary optical cameras having respective fields of view containing said plate.

3. An X-ray apparatus as claimed in claim 1 wherein said means for determining extrinsic imaging parameters include an image pick-up device mounted at one of said X-ray source and said X-ray receiver and a plurality of detectable items, detectable by said image pick-up device, that are stationary relative to said X-ray system.

4. An X-ray apparatus as claimed in claim 1 wherein said means for determining extrinsic imaging parameters include a transmitting and receiving arrangement for wirelessly propagating waves selected from the group consisting of electromagnetic waves and ultrasound waves, including at least transmitter disposed at one of said X-ray source and said X-ray receiver, and at least one receiver which is stationary relative to said X-ray system.

5. An X-ray apparatus as claimed in claim 1 wherein said means for determining extrinsic imaging parameters includes a transmitting and receiving arrangement for wirelessly propagating waves selected from the group consisting of electromagnetic waves and ultrasound waves, having at least one receiver disposed at one of said X-ray source and said X-ray receiver, and at least one transmitter which is stationary relative to said X-ray system.

6. An X-ray apparatus as claimed in claim 1 wherein said X-ray positive marks are disposed substantially in one plane.

7. An X-ray apparatus as claimed in claim 1 further comprising an X-ray transparent marker plate, at which said X-ray positive marks are disposed, which is disposed relative to said X-ray source so that said X-ray beam passes through said X-ray transparent marker plate in said 2D projections.

8. An X-ray apparatus as claimed in claim 7 wherein each of said 2D projections has image corners, and wherein said marker plate has at least three of said X-ray positive marks arranged thereon so that said at least three X-ray positive marks are respectively shown in different image corners of each 2D projection.

9. An X-ray apparatus as claimed in claim 7 wherein each of said 2D projections has image margins, and wherein said marker plate has at least three of said X-ray positive marks arranged thereon so that said at least three X-ray positive marks are respectively shown in different image margins of each 2D projection.

10. An X-ray apparatus as claimed in claim 1 wherein said X-ray positive marks have a shape selected from the group consisting of spheres and rods.

11. An X-ray apparatus as claimed in claim 1 wherein said X-ray source includes a diaphragm having diaphragm edges which limit a cross-section of said X-ray beam, said diaphragm edges representing an image margin in each 2D projection, and said diaphragm edges comprising linear X-ray positive marks.

12. An X-ray apparatus as claimed in claim 11 wherein said diaphragm edges have structures which are imaged in each 2D projection.

13. An X-ray apparatus as claimed in claim 1 wherein said X-ray system includes a C-arm at which said X-ray source and said X-ray receiver are mounted.

14. An X-ray apparatus as claimed in claim 1 wherein said X-ray system is a portable X-ray system.

15. A method for operating an X-ray apparatus comprising the steps of:

displacing an X-ray examination system, having an X-ray source which emits an X-ray beam from a focus and an X-ray detector on which said X-ray beam is incident, relative to an examination subject while irradiating said examination subject with said X-ray beam from a plurality of different projection angles for obtaining a plurality of 2D projection images of said examination subject respectively at said plurality of different projection angles, each of said 2D projection images having a unique projection geometry associated therewith;

determining extrinsic imaging parameters for each of said 2D projection images;

determining intrinsic imaging parameters for each of said 2D projection images by disposing a plurality of X-ray positive marks in a path of said X-ray beam, and irradiating said X-ray positive marks with X-ray beam while irradiating said examination subject from said different projection angles, and causing said X-ray positive marks to follow displacement of said X-ray examination system relative to said examination subject; and determining the respective unique projection geometries for said 2D projection images using said extrinsic imaging parameters and said intrinsic imaging parameters, and, using said 2D projection images and said respective projection geometries, constructing a 3D image therefrom of said examination subject.

16. A method as claimed in claim 15 comprising determining said intrinsic image parameters while obtaining said 2D projection images.

17. A method as claimed in claim 15 comprising obtaining said intrinsic imaging parameters in a calibrating procedure prior to obtaining said 2D projection images.

18. A method as claimed in claim 15 comprising determining said extrinsic image parameters while obtaining said 2D projection images.

19. A method as claimed in claim 15 comprising obtaining said extrinsic imaging parameters in a calibrating procedure prior to obtaining said 2D projection images.

* * * * *